United States Patent [19]

Hallgren

[11] 4,221,920
[45] Sep. 9, 1980

[54] AROMATIC SALICYLATE PROCESS

[75] Inventor: John E. Hallgren, Scotia, N.Y.

[73] Assignee: General Electric Company, Schenectady, N.Y.

[21] Appl. No.: 834,534

[22] Filed: Sep. 19, 1977

Related U.S. Application Data

[63] Continuation of Ser. No. 731,443, Oct. 12, 1976, abandoned.

[51] Int. Cl.² .................................................. C07C 9/84
[52] U.S. Cl. ..................................... 562/406; 560/71; 562/466; 562/467; 562/469; 260/463
[58] Field of Search ..................... 260/473.6; 560/71; 562/406

[56] References Cited

U.S. PATENT DOCUMENTS

| | | | |
|---|---|---|---|
| 3,769,324 | 10/1973 | Paulik et al. | 260/476 |
| 4,096,168 | 6/1978 | Hallgren | 260/463 |
| 4,096,169 | 6/1978 | Chalk | 260/463 |

FOREIGN PATENT DOCUMENTS 1505291 12/1967 Japan.

*Primary Examiner*—Paul J. Killos
*Attorney, Agent, or Firm*—F. Wesley Turner; James C. Davis, Jr.; Joseph T. Cohen

[57] ABSTRACT

An aromatic salicylate process comprising contacting a phenol, carbon monoxide, a base, a Group VIIIB element selected from ruthenium, rhodium, palladium, osmium, iridium or platinum and recovering at least a portion of an aromatic salicylate. The resulting aromatic salicylates are useful in plastics and lacquers as well as in pharmaceuticals.

20 Claims, No Drawings

AROMATIC SALICYLATE PROCESS

CROSS REFERENCE TO RELATED APPLICATIONS

This is a continuation of application Ser. No. 731,443, filed Oct. 12, 1976, now abandoned, which in turn is related to my copending U.S. Pat. application Ser. Nos. 731,494, filed Oct. 12, 1976 and 731,493, filed Oct. 12, 1976, filed concurrently herewith and Alan J. Chalk's U.S. patent application Ser. Nos. 731,496, filed Oct. 12, 1976 and 731,495, filed Oct. 12, 1976 filed concurrently herewith. All of the aforesaid applications are assigned to the same assignee as the assignee of this application.

BACKGROUND OF THE INVENTION

1. Field of the Invention

This invention relates to an aromatic salicylate process comprising contacting a phenol, carbon monoxide, a base, a Group VIIIB element selected from ruthenium, rhodium, palladium, osmium, iridium or platinum and recovering at least a portion of an aromatic salicylate.

2. Description of the Prior Art

A. J. Chalk recognized—as broadly disclosed in the Chalk patent applications referenced herein—that aromatic carbonates can be prepared by contacting a phenol, carbon monoxide, a base, and a Group VIIIB element selected from ruthenium, rhodium, palladium, osmium, iridium or platinum having an oxidation state greater than zero.

Although A. J. Chalk recognized that aromatic carbonates could be formed, Chalk did not recognize that under some process parameters encompassed by Chalk's aromatic carbonate process not only where aromatic carbonates formed but concurrently aromatic salicylates were also formed.

DESCRIPTION OF THE INVENTION

This invention embodies an aromatic salicylate process comprising contacting a phenol, carbon monoxide, a base, and a Group VIIIB element selected from ruthenium, rhodium, palladium, osmium, iridium or platinum and recovering at least a portion of an aromatic salicylate.

The reactants and the resulting reaction products of my process can be illustrated by the following general equations which are furnished for illustrative purposes only since the reaction mechanisms involved in the preparation of aromatic salicylates (Eq. 1) may be much more complex.

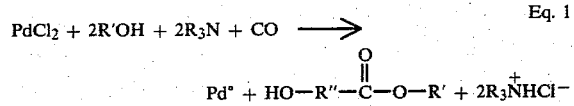

Eq. 1 wherein R is an alkyl radical (including cycloalkyl), R' is an aryl radical, and R" is an arylene radical.

Any of the phenols—subject to the proviso that the phenol have at least one ortho-positioned hydrogen atom relative to an —OH radical attached directly to an aromatic ring carbon atom, solvents, bases, ligands, the Group VIIIB elements, oxidants including oxygen, redox agents, or reaction parameters relative to time, temperature and pressure disclosed in A. J. Chalk's Ser. No. 731,495 or my Ser. No. 731,494 copending applications referenced herein can be employed in my process. Accordingly, their descriptions are hereby incorporated herein in their entirety by reference. Also, any of the amounts disclosed in the aforementioned applications relative to the aforementioned phenols, solvents, etc. can also be employed in a like manner in my process and accordingly the definition of such amounts are also incorporated herein in their entirety also by reference.

The reaction parameters of my process comprise any of Chalk's process parameters, however also include the recovery of an aromatic salicylate.

To optimize the yield of aromatic salicylate a preferred process parameter of my invention comprises delaying the addition of carbon monoxide until the phenolic reactant, Group VIIIB elements and base, have formed a salicylate preliminary reaction admixture, i.e. "salicylate PRM."

In order to optimize the yield of aromatic salicylate, a more preferred process parameter comprises contacting a phenolic reactant with a Group VIIIB element having an oxidation state of at least +2 with a base prior to contacting a previously formed resulting "salicylate PRM" with carbon monoxide. In addition, preferably my process is carried out under reaction conditions which exclude from the reaction media halides, i.e. chloride, bromide, iodide or fluoride, in amounts which are in excess of the amount theoretically required to form a Group VIIIB metal halide salt.

My preference of delaying the introduction or addition of halides and/or carbon monoxide to a "salicylate PRM" until formation of the "salicylate PRM" is a result of my finding that the order of addition and type of reactants employed in my process significantly affects the formation of aromatic salicylates. The significance of the order of addition further exemplified when this disclosure is read in conjunction with the disclosure of my previously referred to U.S. patent application Ser. No. 731,493.

Preferred phenolic reactants are phenols containing from 6 to 30, and more preferably from 6 to 15 carbon atoms. Illustrative of commercially important phenolic reactants included within the above description are the following: phenol itself (hydroxy benzene); napthol; ortho-, meta-, or paracresol; catechol; meta, para-xylenol; resorcinol; the various isomers of dihydroxydiphenyl; the isomers of dihydroxynapthalene; bis(4-hydroxyphenyl)propane-2,2; α,α'-bis(4-hydroxyphenyl)-p-diisopropylbenzene; 4,4'-dihydroxy-3; 5,3'-trichlorophenylpropane-2,2; 4,4'-dihydroxy-3,5,3'-tribromophenylpropane-2,2; phloroglucinol, dihydroxy oligomers, for example an oligomer derived from bisphenol-A, etc.

A generally preferred bisphenol that can be used in my process can be described by the following formula:

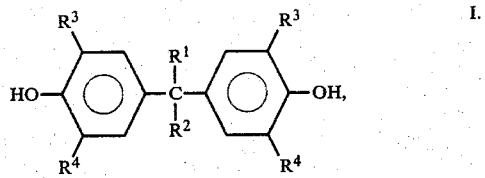

I.

where $R^1$ and $R^2$ are hydrogen, $C_{1-4}$ alkyl or phenyl, and at least one of $R^3$ or $R^4$ is hydrogen. Another preferred bisphenol comprises formula I where $R^1$ and $R^2$ are as defined before and at least one of $R^3$ is hydrogen and the other is hydrogen or $C_{1-4}$ alkyl, and at least one of $R^4$ is hydrogen and the other is hydrogen or $C_{1-4}$ alkyl. Especially preferred is bis(4-hydroxyphenyl)propane-2,2, also commonly known as "bisphenol-A" (BPA).

Illustrative of the generally preferred Group VIIIB element compounds or complexes that can be used in my process follow: $RuCl_2$, $RuBr_2$, $RuI_2$, $Ru(CO)_2Cl_2$, $Ru(CO_2I_2$, $Ru(CO)_4Cl_2$, $Ru(CO)_4Br_2$, $Ru(CO)_4I_2$, $RuCl_3$, $RuBr_3$, $RuI_3$, etc., $PdCl_2$, $PdBr_2$, $PdI_2$, $[Pd(CO)Cl_2]_2$, $[Pd(CO)Br_2]_2$, $[Pd(CO)I_2]_2$, $(C_6H_5CN)_2PdCl_2$, $PdCl_4$, $Pd(OH)_2(CNC_4H_9)_2$, $PdI_2(CNC_6H_5)_2$, $Pd(OH)_2(CNCH_3OC_6H_5)_2$, $Pd(CNC_4H_9)_4$, etc.; $Rh(CO)Cl_2$, $Rh(CO)Br_2$, $Rh(CO)I_2$, $Rh_2Cl_2(CO)_2$, $Rh_2(CO)_4Cl_2$, $Rh_2(CO)_4Br_2$, $Rh_2(CO)_4I_2$, $[Rh(CO)_2Cl]_2$, $RhCl_3$, $RhBr_3$, $RhI_3$, etc.; $Os(CO)_3Cl_2$, $Os(CO)_3Br_2$, $Os(CO)_3I_2$, $Os(CO)_4Cl_2$, $Os(CO)_4Br_2$, $Os(CO)_4I_2$, $Os(CO)_8Cl_2$, $Os(CO)_8Br_2$, $Os(CO)_8I_2$, $OsCl_2$, $OsCl_3$, $OsI_2$, $OsI_3$, $OsBr_3$, $OsBr_4$ and $OsCl_4$, etc.; $IrCl_3$, $IrCl_3(CO)$, $Ir_2(Co)_8$, $IrCl_3$, $IrBr_3$, $IrCl_3$, $IrBr_4$, $IrI_4$, etc.; $PtCl_2$, $PtBr_2$, $PtI_2$, $Pt(CO)_2Cl_2$, $Pt(CO)_2Br_2$, $Pt(CO)_2I_2$, $Pt(CO)_2Cl_4$, $Pt(CO)_2Br_4$, $Pt(CO)_2I_4$, $Pt(CO)_3Cl_4$, $Pt(CO)_3Br_4$, $Pt(CO)_3I_4$, $PtCl_2(CNC_6H_5)_2$, etc.

Preferred bases are sterically hindered amines, e.g. diisopropylmonoethylamine, 2,2,6,6,N-pentamethylpiperidine, etc.

In my process any amount of base can be employed. In general, effective mole ratios of base to the Group VIIIB elements are within the range of from about 0.00001:1 to about 100:1 or higher, preferably from 0.5:1 to about 10:1, and more preferably from 1:1 to 2:1. Generally, wherein my process is carried out in accord with any of the preferred process parameters described herein before, mole ratios of at least 1:1 enhance both the reaction rate and the yield of aromatic salicylate.

In my process, presently preferred carbon monoxide pressures are within the range of from 1 to 200 atmospheres.

In my process solvent, preferably inert, to phenolic reactant mole proportions are preferably from 50:50 to 99:1.

Any reaction temperature can be employed. In general, optimum reaction temperatures are 0° C., or even lower to 300° C., or even higher.

In still another process parameter of my invention, my process is carried out under catalytic reaction conditions employing an oxidant including oxygen, a redox agent and a drying agent at reaction temperatures in excess of 100° C., more preferably 150° C. and even more preferred 200° C., since optimum yields of aromatic salicylate are obtained under these reaction conditions. The oxidants, redox agents and drying agents that can be used under the aforementioned preferred reaction conditions are described in detail in A. J. Chalk's Ser. No. 731,495 and my Ser. No. 731,494 applications. The descriptions of oxidants, redox agents and drying agents set out in the above-referenced applications are hereby incorporated herein in their entirety by reference. Particularly preferred in the preparation of aromatic salicylates at elevated temperatures is the use of an oxidant selected from manganese or cobalt complexes and molecular sieve drying agents. A description of preferred manganese and cobalt complexes and molecular sieves is set out in my Ser. No. 731,494 application, and this description is incorporated herein in its entirety by reference.

In my process whenever either air or gaseous oxygen is employed, preferably pressures within the range of from about ½ to 200 atmospheres are employed.

The aromatic salicylates of my invention can be generically described by the following formula:

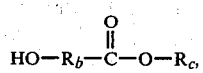

wherein $R_b$ represents an aromatic radical wherein the hydroxyl radical is positioned ortho relative to the carboxylate, i.e.

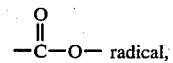

and $R_c$ represents an aromatic radical. The $R_b$ and $R_c$ radicals can be carbo- or hetero-monocyclic, polycyclic, of fused polycyclic, and can have two or more cyclic systems (monocyclic, polycyclic or fused polycyclic systems) which are directly joined to each other by single or double valence bonds, or by bi- or multivalent radicals.

In order that those skilled in the art may better understand my invention, the following examples are given which are illustrative of the best mode of this invention, however, these examples are not intended to limit the invention in any manner whatsoever. In the examples, unless otherwise specified, all parts are by weight and the reaction products were verified by infrared spectrum, C-13 nuclear magnetic resonance and mass spectrometry.

EXAMPLE I

Preparation of phenyl salicylate using hydroxybenzene carbon monoxide, diisopropylmonoethylamine and bis(benzonitrile)palladium(II) dichloride.

A reaction vessel was charged with 1.50 g. (4.0 mml.) of bis(benzonitrile)palladium(II) dichloride, 0.77 g. (8.0 mmol.) of phenol, and 10 ml. of methylene chloride. The mixture was stirred, flushed slowly with carbon monoxide, and 1.5 g. (11.6 mmol.) of diisopropylmonoethylamine was added. The solution immediately turned black and palladium metal precipitated. After stirring at room temperature for three hours, the mixture was filtered. The precipitate was washed with methylene chloride, then dried in a stream of air, to yield 0.43 g. (101%) of palladium metal. The filtrate was analyzed and the presence of 0.23 g. (52% yield) of diphenyl carbonate and 0.45 g. (53%) of phenyl salicylate of the formulas, respectively, was formed:

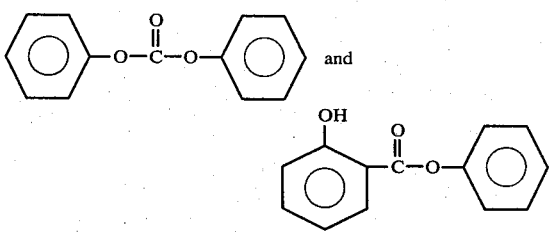

EXAMPLE II

Preparation of 4'-methylphenyl-2-hydroxy-5-methyl benzoate using 4-methylphenol as the phenolic reactant.

A reaction vessel was charged with 0.77 g. (2.0 mmol.) of bis(benzonitrile)palladium(II) dichloride, 7 ml. of methylene chloride, and a solution of 0.22 g. (2.0 mmol.) of 4-methylphenol plus 0.52 g. (4.0 mmol.) of diisopropylmonoethylamine dissolved in 5 ml. of methylene chloride. Carbon monoxide was bubbled through the solution for two hours. The analysis of the products was 0.15 g. (60%) of 4,4'-dimethyldiphenyl carbonate and 0.18 g. (38%) of 4'-methylphenyl-2-hydroxy-5-methyl benzoate of the formulas, respectively:

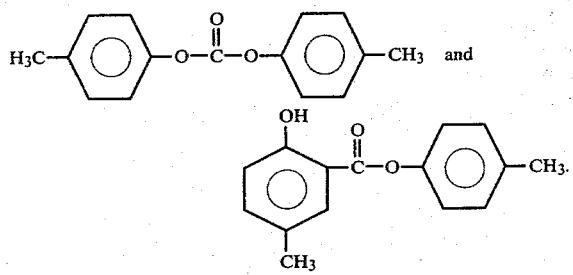

EXAMPLE III

Preparation of 4-(α,α-dimethylbenzyl)phenyl 5-(α,α-dimethylbenzyl)-2-hydroxybenzoate using p-cumyl phenol as the phenolic reactant.

A reaction vessel was charged with 0.77 g. (2.0 mmol.) of bis(benzonitrile)palladium(II) dichloride, 7 ml. of methylene chloride, and a solution of 0.42 g. (2.0 mmol.) of p-cumylphenol plus 0.52 g. (4.0 mmol.) of diisopropylmonoethylamine dissolved in 7 ml. of methylene chloride. The mixture was stirred to effect solution and carbon monoxide bubbled through the solution overnight. Subsequent work-up showed the presence of 0.32 g. (71% yield) of 4,4'-(α,α-dimethylbenzyl)diphenyl carbonate and 0.18 g. (20%) of 4-(α,α-dimethylbenzyl)phenyl 5-(α,α-dimethylbenzyl)-2-hydroxybenzoate of the formulas, respectively:

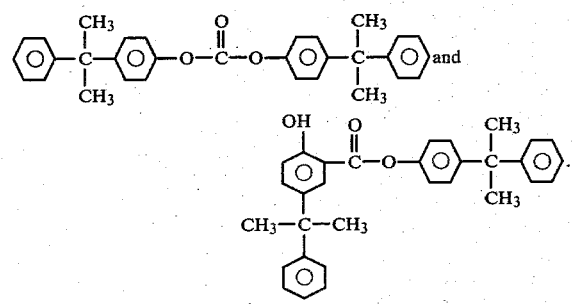

EXAMPLE IV

Preparation of 4'-methylphenyl-2-hydroxy-5-methyl benzoate under pressure.

The reaction medium contained 4.03 g. (1.05 mmol.) of bis(benzonitrile)palladium(II) dichloride, 20 ml. of methylene chloride, 0.108 g. of 4-methylphenol, 1.131 g. of diisopropylmonoethylamine, and sufficient carbon monoxide to charge the vessel to 65 psi. The product yield was 38% of 4,4'-dimethyldiphenyl carbonate and 41% of 4'-methylphenyl-2-hydroxy-5-methyl benzoate.

EXAMPLE V

Preparation of 4'-methylphenyl-2-hydroxy-5-methyl benzoate using palladium(II) dichloride.

A reaction vessel was charged with 10 ml. of methylene chloride, 0.108 g. (1.0 mmol.) of 4-methylphenol, 0.137 g. (1.1 mmol.) of diisopropylmonoethylamine, and sufficient carbon monoxide to pressure the vessel to 65 psi. 0.199 g. (1.12 mmol.) of palladium(II) dichloride, i.e. PdCl$_2$, was added. The product yield was 0.98 g. (81% of 4,4'-dimethyldiphenyl carbonate and 0.08 g. (7%) of 4'-methylphenyl-2-hydroxy-5-methyl benzoate.

EXAMPLE VI

Preparation of 4'-methylphenyl-2-hydroxy-5-methyl benzoate using 4-methyl sodium phenoxide as the base.

The reaction vessel contained 0.184 g. (1.04 mmol.) of palladium(II) dichloride, 10 ml. of methylene chloride, 0.125 g. (1.16 mmol.) of 4-methylphenol, 0.080 g. (0.62 mmol.) of 4-methyl sodium phenoxide and sufficient carbon monoxide to charge the vessel to 63 psi. The product yield was 5% of 4,4'-dimethyldiphenyl carbonate and 8% of 4'-methylphenyl-2-hydroxy-5-methyl benzoate.

EXAMPLE VII

Preparation of 4'-methylphenyl-2-hydroxy-5-methyl benzoate using potassium carbonate as a base.

The reaction vessel contained 0.182 g. (1.03 mmol.) of palladium(II) dichloride, 10 ml. of methylene chloride, 0.233 g. (2.16 mmol.) of 4-methylphenol, 0.320 g. (2.32 mmol.) of potassium carbonate and sufficient carbon monoxide to charge the vessel to 64 psi. The product yield was 5% of 4,4'-dimethyldiphenyl carbonate and 1% of 4'-methylphenyl-2-hydroxy-5-methyl benzoate.

EXAMPLE VIII

Preparation of 4'-methylphenyl-2-hydroxy-5-methyl benzoate using potassium fluoride as a base.

The reaction vessel contained 0.182 g. (1.00 mmol.) of palladium(II) dichloride, 10 ml. of methylene chloride, 0.248 g. (2.3 mmol.) of 4-methylphenol, 0.150 g. (2.6 mmol.) of potassium fluoride, and sufficient carbon monoxide to charge the vessel to 65 psi. The product yield was 3% of 4,4'-dimethyldiphenyl carbonate and 1% of 4'-methylphenyl-2-hydroxy-5-methyl benzoate.

EXAMPLE IX

Preparation of phenyl salicylate using rhodium(III) trichloride.

A reaction vessel was charged with 4 g. (42.0 mmol.) of hydroxybenzene and 0.83 g. (4.0 mmol.) of rhodium trichloride, i.e. RhCl$_3$. The mixture was warmed to 100° C., carbon monoxide was bubbled through the mixture and 2.5 g. (16.0 mmol.) of 2,2,6,6,N-pentamethylpiperidine was added. Subsequent workup and analysis showed the presence of diphenylcarbonate (estimated yield 1%) and 0.7 g. (8%) of phenyl salicylate.

EXAMPLES X-XIII

Preparation of phenylsalicylate using a preliminary reaction admixture, i.e. phenol, carbon monoxide and bis(benzonitrile)palladium(II)dichloride and regulating relative to time the order of addition of a base, e.g. diisopropylmonoethylamine, to the preliminary reaction admixture.

A series of independent reactions were carried out wherein a preliminary reaction admixture, i.e. a "PRM," was contacted with a base, i.e. diisopropylmonoethylamine, 5, 20, 60 and 120 minutes after the PRM was initially contacted with carbon monoxide. A control run was carried out with base being added at zero minutes, e.g. essentially simultaneously with the formation of the PRM. Three hours after the combination of the PRM ingredients, the resulting reaction products were analyzed and the relative proportions of diphenylcarbonate and phenylsalicylate were determined. Summarized in Table I are the reaction parameters and products, i.e. the time of addition of the base to the PRM and the resulting reaction products, i.e. the diphenylcarbonate and the phenylsalicylate.

TABLE I

| Example No. | Run No. | Base Addition Time (min) | Relative Proportions diphenylcarbonate:phenylsalicylate |
| --- | --- | --- | --- |
| Control | 1.* | 0 | 0.05:99.95 |
| X | 2. | 5 | 0.25:99.75 |
| XI | 3. | 20 | 5:95 |
| XII | 4. | 60 | 50:50 |
| XIII | 5. | 120 | 100: 0 |

*control run

As illustrated by this example, the time and "order of addition" sequence, i.e. time and order of addition of base to a PRM in the practice of my process significantly effects the relative proportions and accordingly the yields of diphenylcarbonate and phenylsalicylate obtained.

EXAMPLE XIV

Preparation of phenyl salicylate using palladium(II) dichloride as the Group VIIIB compound and copper-(II)dichloride as the oxidant under carbon monoxide pressure.

A reaction vessel was charged with 94 g. (1.0 mole) of phenol, 34.0 g. (0.25 mol) of copper(II)dichloride, 0.45 g. (0.0025 mol) of palladium(II)dichloride, 147 g. (0.75 mol) of dicyclohexyl-N-methylamine, and 500 ml. of methylene chloride. The mixture was pressurized with 420 psig CO and heated to 160° C. for 4 hours, cooled and vented. Gas chromatography established the presence of 10.7 g. of phenyl salicylate (5% conversion based on phenol, 40% yield based on $CuCl_2$).

In the practice of my process, the Group VIIIB elements after separation from the resulting reaction products can be oxidized or reduced to any suitable oxidation state, and can be re-employed, that is, recycled in the aromatic salicylate process described herein.

Although the above examples have illustrated various modifications and changes that can be made in the carrying out of my process, it will be apparent to those skilled in the art that other Group VIIIB metals, phenolic compounds, ligands, oxidants, redox components, drying agents and solvents as well as other reaction conditions can be effected without departing from the scope of the invention.

I claim:

1. An aromatic salicylate process which comprises contacting sequentially the following reactant groups:
   (a) a phenol, a base, and a Group VIIIB element selected from ruthenium, rhodium, palladium, osmium, iridium or platinum having an oxidation state of at least +2, and subsequently
   (b) carbon monoxide.
2. The claim 1 process, wherein the temperature is within the range of from 0° C. to 300° C.
3. The claim 2 process wherein the temperature range is from 0° C. to 200° C.
4. The claim 3 process wherein the temperature range is from 0° C. to 100° C.
5. The claim 4 process wherein the temperature range is from 0° C. to 50° C.
6. The claim 1 process, wherein said base is a tertiary amine.
7. The claim 1 process, wherein the salicylate: carbonate proportions are within the range of from 100:0 to about 50:50.
8. The claim 1 process, wherein the salicylate: carbonate proportions are from about 99.95:0.05 to about 95:5.
9. The claim 1 process, wherein said element is present in an ionic form.
10. The claim 1 process, wherein said element oxidation state is +2.
11. The claim 1 process, wherein said base is a sterically hindered amine.
12. The claim 1 process, wherein said element is associated with a carbonyl group.
13. The claim 1 process, wherein said element is associated with a halide.
14. The claim 1 process, wherein said element is coordinated with a ligand selected from a nitrile or a halide.
15. The claim 1 process, wherein said element is associated with an inorganic halide compound.
16. The claim 1 process, wherein methylene chloride is employed as a solvent, the base is diisopropylmonoethylamine, the phenol is 4-methylphenol, the Group VIIIB element is palladium in the form of palladium(II) dichloride.
17. The claim 1 process, in which said salicylate is prepared in a methylene chloride solution in which the base is diisopropylmonoethylamine, the phenol is phenol, and the Group VIIIB element is palladium in the form of bis(benzonitrile)palladium(II) dichloride.
18. The claim 1 process, further comprising, after the preparation of the aromatic salicylate, separating at least a portion of any resulting Group VIIIB element or compound from said salicylate, oxidizing at least a portion of said resulting Group VIIIB element or compound to an oxidation of at least +2, and recycling at least a portion of said oxidized element in said aromatic salicylate process.
19. The claim 1 process, wherein the element is palladium.
20. The claim 18 process, wherein the element is palladium.

* * * * *